United States Patent [19]

Giacometti

[11] Patent Number: 5,709,829
[45] Date of Patent: Jan. 20, 1998

[54] METHOD FOR MANUFACTURING PRODUCT IN MEMBRANE OR FILM FORM

[75] Inventor: Claudio Giacometti, Pistoia, Italy

[73] Assignee: PANTEX S.r.l., Pistoia, Italy

[21] Appl. No.: 676,885

[22] Filed: Jul. 8, 1996

Related U.S. Application Data

[63] Continuation of Ser. No. 433,679, May 4, 1995, abandoned, and a continuation of Ser. No. 151,562, Nov. 12, 1993, abandoned.

[30] Foreign Application Priority Data

Nov. 17, 1992 [EP] European Pat. Off. .............. 92830624

[51] Int. Cl.⁶ .......................... B26F 1/18; B26F 1/20
[52] U.S. Cl. ............ 264/156; 83/30; 261/DIG. 48; 425/290; 425/DIG. 119
[58] Field of Search ................... 264/156, 154, 264/DIG. 48, 155; 425/290, 294, DIG. 119, 289; 55/DIG. 5; 83/30

[56] References Cited

U.S. PATENT DOCUMENTS

| | | | |
|---|---|---|---|
| 247,368 | 9/1881 | Lang | 493/321 |
| 404,581 | 6/1889 | Wheeler | 451/55 |
| 1,978,620 | 10/1934 | Brewster | 428/119 |
| 2,218,674 | 10/1940 | Eaton | 451/67 |
| 2,748,863 | 6/1956 | Benton | 264/156 |
| 2,801,501 | 8/1957 | Marogg | 451/70 |
| 2,862,251 | 12/1958 | Kalwaites | 268/119 |
| 2,924,863 | 2/1960 | Chavannes | 264/156 |
| 3,025,585 | 3/1962 | Griswold | 28/106 |
| 3,040,412 | 6/1962 | Russell | 28/104 |
| 3,081,501 | 3/1963 | Kalwaites | 28/106 |
| 3,081,512 | 3/1963 | Griswold | 264/119 |
| 3,081,515 | 3/1963 | Griswold | 428/131 |
| 3,085,608 | 4/1963 | Mathues | 383/103 |
| 3,092,439 | 6/1963 | Harrison | 264/154 |
| 3,101,520 | 8/1963 | George et al. | 264/119 |
| 3,104,998 | 9/1963 | Gelpke | 428/135 |
| 3,137,893 | 6/1964 | Gelpke | 425/290 |
| 3,161,554 | 12/1964 | Blackford | 264/156 |
| 3,227,854 | 1/1966 | Ramsey et al. | 264/156 |
| 3,292,619 | 12/1966 | Egler | 602/47 |
| 3,307,545 | 3/1967 | Surowitz | 602/47 |
| 3,509,007 | 4/1970 | Kalwaites | 428/132 |
| 3,509,607 | 5/1970 | Kalwaites | 428/132 |
| 3,546,742 | 12/1970 | Kugler | 425/290 |
| 3,632,269 | 1/1972 | Doviak et al. | 264/154 |
| 3,703,432 | 11/1972 | Koski | 264/156 |

(List continued on next page.)

FOREIGN PATENT DOCUMENTS

| | | |
|---|---|---|
| 0502237 A1 | 9/1992 | European Pat. Off. . |
| 502237 | 9/1992 | European Pat. Off. . |
| 484929 | 5/1938 | United Kingdom . |
| 1270777 | 4/1972 | United Kingdom . |

OTHER PUBLICATIONS

"Formed Films—The Hole Story" by William Ouellette presented at the IMPACT '86 Conference in Bal Harbour, Florida—Mar. 16–18, 1986.

"A New Coverstock for Disposable Products" by R. E. Cornelissen at the Edana's 1985 Milan Nonwovens Symposium at Milan, Italy.

"Apertured Film—The 'Other' Nonwoven" by Francis J. Bouda presented at the INDEX '96 Congress in Geneva, Switzerland—Feb. 13–16, 1996.

*Primary Examiner*—Duane S. Smith
*Attorney, Agent, or Firm*—Breiner & Breiner

[57] ABSTRACT

A method for forming a web (N) that is permeable to liquids and designed to separate two environments and to allow the liquid to flow in one direction from one of said environments to the other. The web is caused to pass between two contra-rotating cylinders (5, 7) that are pressed against each other, one of said cylinders (7) having a surface provided with projections which cause perforations in said web (N). The cylinder (7) with the projections is turned at a peripheral speed greater than the peripheral speed of the other cylinder (5), with a consequent relative slipping action between the surfaces of the two cylinders (5, 7).

4 Claims, 2 Drawing Sheets

U.S. PATENT DOCUMENTS

| | | | |
|---|---|---|---|
| 4,276,336 | 6/1981 | Sabee | 264/154 |
| 4,280,978 | 7/1981 | Dannheim et al. | 264/DIG. 48 |
| 4,377,544 | 3/1983 | Rasmussen | 264/154 |
| 4,568,596 | 2/1986 | Johnson | 62/197 |
| 4,780,352 | 10/1988 | Palumbo | 428/138 |
| 4,842,794 | 6/1989 | Hovis et al. | 264/154 |
| 4,859,519 | 8/1989 | Cabe, Jr. et al. | 264/156 |
| 4,886,632 | 12/1989 | Van Iten et al. | 264/154 |

METHOD FOR MANUFACTURING PRODUCT IN MEMBRANE OR FILM FORM

This application is a continuation of application Ser. No. 08/433,679, filed May 4, 1995, now abandoned and a continuation of application Ser. No. 08/151,562 filed Nov. 12, 1993, now abandoned.

BACKGROUND OF THE INVENTION

The invention relates to a method for forming a composite membrane, film or web of a material designed to form, for example, the outer layer of a sanitary towel, nappy or other product, for example a filtering device. In particular, the invention relates to a method in which the composite membrane or film or web is perforated to produce holes for the liquid which is to penetrate from the outside of the absorbent into the body of material contained in said absorbent.

More generally, the invention relates to a method for manufacturing a membrane or film of perforated material designed to separate two environments between which a liquid must be caused to flow in one direction, but not in the opposite direction. In the course of the following description, reference will be made especially to nappies or sanitary towels. However, it should be emphasised that the product produced by the method of the present invention may be used wherever there is a need for a membrane to be permeable to a liquid which must pass through the membrane or film in one direction only, as for example in a filtering device.

U.S. Pat. No. 4,780,352 discloses a product consisting of a nonwoven membrane with a plurality of holes distributed across the whole membrane to enable the liquid to pass through it. According to this patent, the material is perforated by passing it between two contra-rotating rollers whose peripheral speeds are equal to each other and to the speed of advance of the material itself. One of the two rollers comprises projections which perforate the material in cooperation with the other roller.

OBJECT OF THE INVENTION

The object of the present invention is to provide a method and an apparatus for forming a membrane and/or web and/or film making it possible to achieve a particular configuration of the holes in such a way as to direct the flow of liquid, so that it can penetrate, for example from the outside to the inside of the absorbent, but cannot then leak out of the latter.

A further object of the present invention is to provide a method for making a membrane and/or film that will efficiently isolate the material inside the absorbent away from the user's skin.

A further object of the present invention is to provide a method and apparatus for manufacturing a product in membrane or film or composite form, able to form a barrier to delimit and separate two environments, between which a liquid must flow in one direction, but not in the opposite direction.

SUMMARY OF THE INVENTION

In essence, according to the method of the invention, the membrane and/or film is passed between a first rotating cylinder whose surface is essentially smooth and a second rotating cylinder whose surface is studded, that is it has a series of protuberances, and is pressed against the first cylinder, the peripheral speed of the smooth cylinder and the speed of advance of the membrane and/or film material being less than the peripheral speed of the studded cylinder. This produces a slipping action whose effect on the material is to create holes by plastic deformation of the film material with a consequent but only partial detachment of the material in the holes and creation of strands of partially detached material lying in the direction in which the membrane material is fed through the two cylinders. The function of these strands is to allow the liquid to pass from one side of the membrane and/or film material to the other (more particularly, from the side on which the studded cylinder has acted towards the side that has passed in contact with the smooth cylinder) preventing the liquid from flowing back in the opposite direction.

The method according to the invention may advantageously be used with web materials of low basis weight, for example between 8 and 80 gsm. The membrane or film processed by the method of the present invention may be formed by a single membrane of nonwoven, for example of carded fibers, or of woven textile fibres (with suitable hydrophobic properties) or a plastic film. The method may also be employed on composite materials, consisting for example of two or more membrane of carded fibers or composites consisting of fibre membranes stuck to plastic film. Typically, it is possible to use a plastic film to each side of which a membrane of carded fibers has been applied. Firm sandwiching together of the layers forming the material can be achieved by the same rolling and slipping action used to create the special perforations described above.

Since the holes (and hence the strands) are very close together, the method of the present invention produces a membrane whose overall thickness may be much greater than the thickness of the initial material. For example, starting with a thickness of the membrane or film of 30 micrometers, it is possible to reach an overall thickness of 300 micrometers. This makes it possible, with a very small amount of material, to produce a membrane that is very thick and hence has very good isolating properties. This advantage is especially evident if a single, that is non-composite, film or membrane is used.

In an especially advantageous embodiment, and in particular for the efficient processing of plastic film material, such as polyethylene and its derivatives or other suitable plastic materials, either one or both of the cylinders may be heated to a suitable temperature. The heat increases the viscosity of the plastic material and hence facilitates its perforation and the deformation of the strands of material partially detached from the base material. Advantageously, the two cylinders can be heated to temperatures that can be adjusted independently of each other. The surface temperature of the cylinder bearing the projections is preferably higher than the temperature of the other cylinder.

The pressure between the two cylinders, and hence the pressure with which the film and/or membrane material is rolled, may advantageously be variable to suit the base material being used. Also the difference in speed, and hence the slipping between the surfaces of the rotating cylinders may vary between preset limits to suit the material being used. More particularly, the slipping may vary advantageously between 10 and 50% and preferably between 15 and 25%. The temperature of the surfaces of the cylinders may advantageously be set at between 70° and 240° C. and in particular between 100° and 180° C. The linear pressure between the rollers may vary between, for example, 120 and 220 kg/cm and preferably between 130 and 150 kg/cm.

To produce semifinished items for use in particular products, for example nappies for babies or incontinent persons, sanitary towels for women, and so forth, according to the method of the invention the material in film and/or membrane form may be perforated along continuous longitudinal strips or else along areas not extending the full length of the web. As a result, in the application of the membrane to the finished product, it is possible to have areas in which the liquid is able to flow (through the holes) from one side to the other, for example towards the inside of the absorbent, and completely impervious areas across which the liquid cannot flow back. The perforated area will of course be positioned on the absorbent over the area where the flow of liquid to be absorbed arrives.

The apparatus according to the invention comprises a pair of rotating cylinders pressing against each other, between which the membrane or web to be processed is passed; a first cylinder being smooth and a second cylinder having projections to produce the perforations. Characteristically the peripheral speed of the cylinder having the projections is greater than the peripheral speed of the smooth cylinder, so that the film and/or membrane material, which is rolled between the two cylinders, is subjected to a slipping action and to a consequent plastic deformation.

Advantageously, either one or both of the cylinders may have heating means to maintain the outer surface at a suitable temperature to facilitate the processing by plastic deformation of the web material. The heating means of the two cylinders are advantageously independently adjustable.

The cylinder with the projections may comprise a series of identical projections over the while cylindrical surface, or in localised areas, for example and in particular over annular areas, to produce a material that is perforated along defined longitudinal strips and with non-perforated areas between one strip and the adjacent strip. To produce a web with perforations over areas bounded by non-perforated areas it is also possible, and preferable, to employ a cylinder with projections of differing heights and optionally of differing shapes, in particular such that the projections are higher in areas to be perforated and lower in areas not to be perforated. In areas with less prominent projections the web is sufficiently well rolled to ensure cohesion between the various optional layers forming the membrane, but is not perforated.

Further characteristics of the apparatus and of the method according to the invention are shown in the accompanying claims.

A clearer understanding of the invention will be obtained from the description and attached drawing, which latter shows a practical, non-restricting embodiment of the said invention. In the drawing:

DESCRIPTION OF THE PREFERRED EMBODIMENT(S)

Figure 1:
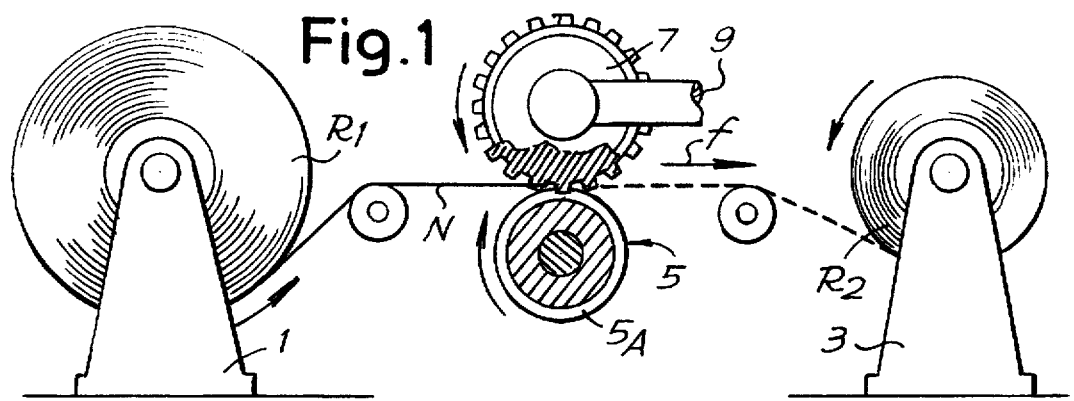
FIG. 1 shows a highly diagrammatic illustration of a possible embodiment of an apparatus according to the invention.

Referring initially to FIG. 1, the apparatus (in this embodiment) has means 1 for supporting a first roll R of web, which may be a plastic film. The web N is wound off the roll R1 and rewound onto a roll R2 carried by support means 3. The support means 3 have a motor (not shown) which turns the roll R2 in order to draw the web N and wind it up. Between the two supports 1 and 3 is a pair of cylinders indicated by 5 and 7 respectively. In the embodiment illustrated, the cylinder 5 is positioned underneath the web N and turns in a clockwise direction. The cylinder 5 has an outer surface defined by a layer 5A of elastically yielding material, for example rubber. This material may be the same as is typically used in equipment for the embossing of paper material in the production of toilet paper and similar products. The possibility of using a cylinder 5 having a steel outer surface is not excluded.

Interacting with the cylinder 5 is the cylinder 7 which turns in an anticlockwise direction. The two cylinders 5 and 7 are pressed against each other with a pressure that advantageously is adjustable. The cylinder 7 is studded, that is it has a worked surface with geometrically distributed projections. Possible shapes for the projections of the cylinder 7 will be described in greater detail when referring to the subsequent FIGS. 2 to 5 and 9.

The cylinder 7 turns with a peripheral speed greater by an adjustable percentage than the peripheral speed with which the underlying roller 5 turns. This creates a relative slipping action between the surfaces of the two cylinders and hence a rolling and slipping action within the web N which is being passed between the two cylinders 5 and 7, with consequent effects on the material which will be illustrated later with reference to FIGS. 6 and 7.

The cylinder 7 may advantageously be maintained at a high temperature, for example by the admission of steam or heat-conducting oil at high temperature through a pipe 9 which communicates with the interior of the cylinder 7 through a suitable rotating joint. Likewise the cylinder 5 may advantageously be heated by a similar system. As an alternative to heating by means of a heat-carrying fluid, the heating may be by means of electrical resistors or any other system suitable for the purpose.

Figure 3:
FIGS. 2 and 3 show a front view and a cross section taken through III—III respectively of a portion of the studded cylinder in one possible embodiment.
Figure 2:
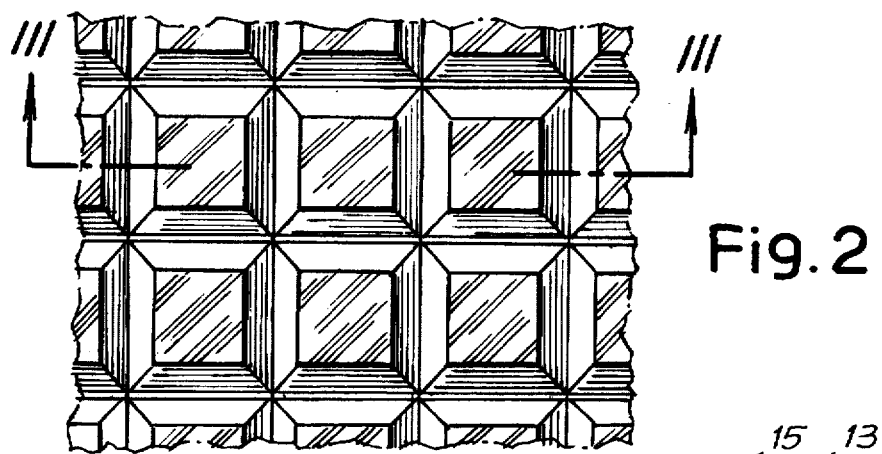
Figure 5:
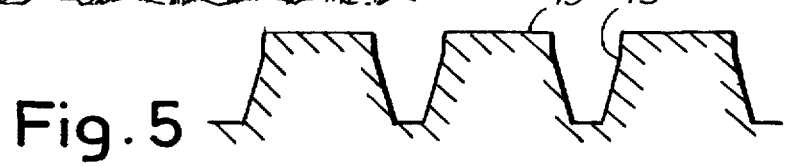
FIGS. 4 and 5 show, in the same way as FIGS. 2 and 3, a different configuration of the surface of the studded cylinder.
Figure 4:
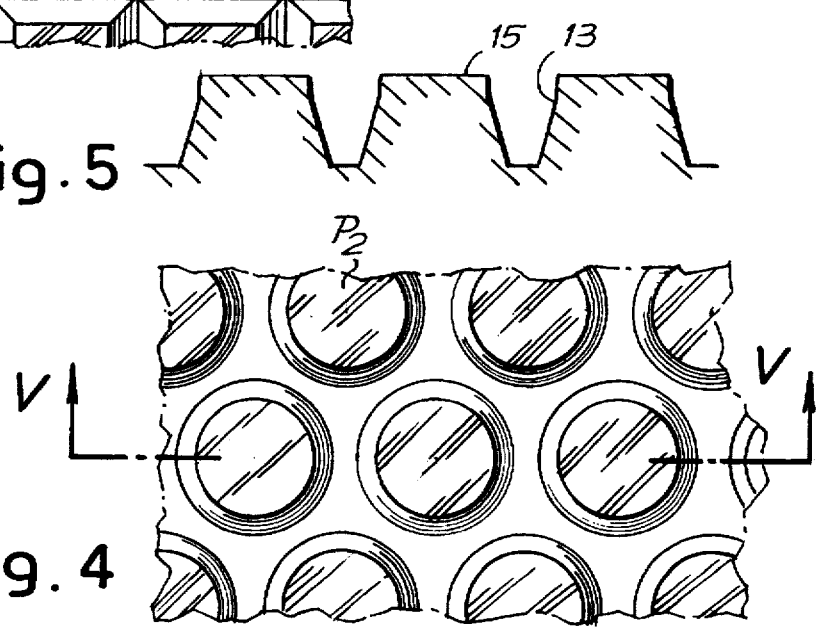

FIGS. 2 and 3 show a possible design for the projections of the cylinder 7. In this embodiment, the cylinder has a grid of frustopyramidal protuberances on a square base, indicated by P1 in FIG. 3. FIGS. 4 and 5 show a different possible form for the projections of the cylinder 7, this form being characterised by protuberances P2 of generally frustoconical shape with a terminal portion 13 of approximately cylindrical form and a front surface 15 which interacts with the smooth surface of the cylinder 5.

Different forms of the studding of the cylinder 7 are also possible. These may be chosen to suit the aesthetic and technical requirements of the end product, and the cost of making the cylinder 7.

Figure 6:
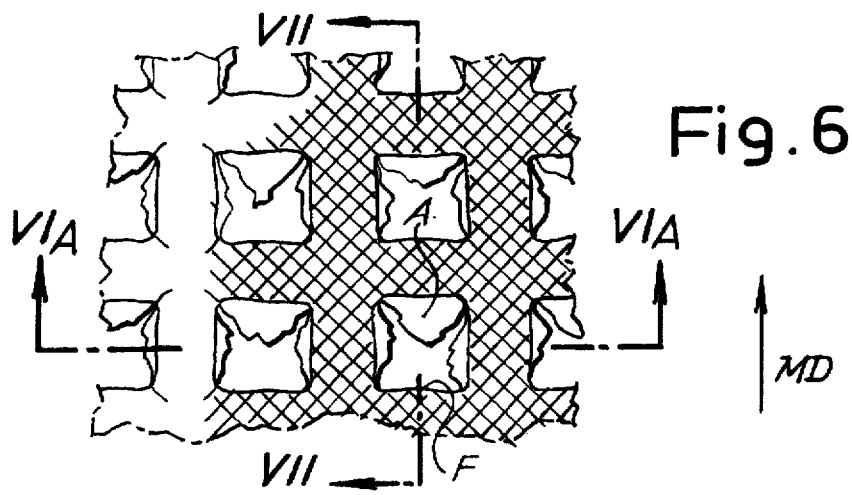
FIGS. 6, 6A and 7 show a portion of product in a plan view, in two cross sections taken along the direction of advance of the material through the apparatus and transversely to the direction of advance, respectively.
Figure 6A:
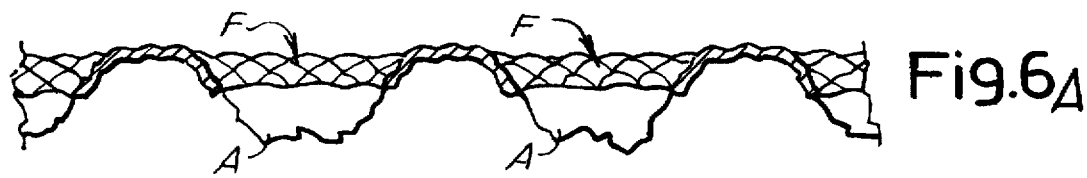
Figure 7:
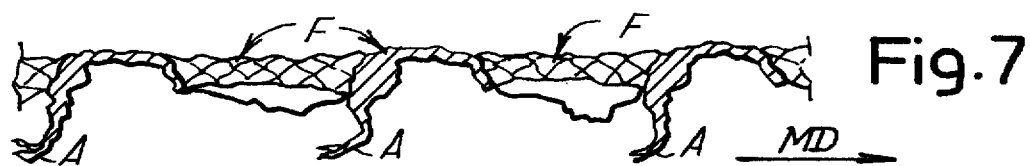
Figures 8, 9:
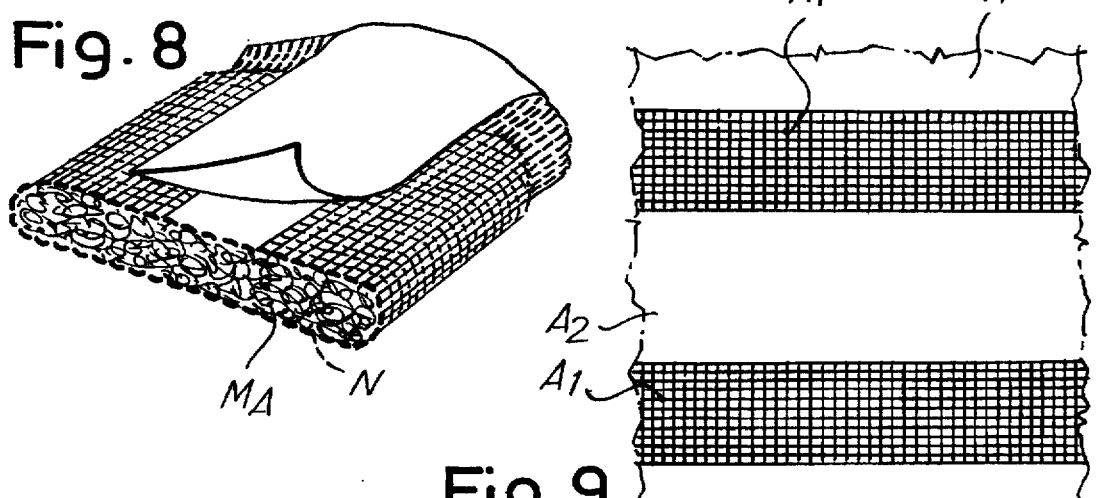
FIG. 8 shows a diagrammatic cross section of an absorbent.
FIG. 9 shows a portion of film or membrane perforated in strips.

As the web N is passed between the cylinders 5 and 7, it undergoes a plastic deformation which results in the perforation of the material as the protuberances P1 or P2 of the cylinder 7 break through it. The material which is detached from the base material forming the web N is not completely removed but remains connected to the base material by at least a portion of the perimeter of the hole and lies in the direction of advance of the web N, that is in the direction of the arrow f shown in FIG. 1. The direction in which the partially detached material in each hole lies is determined by the relative slipping action between the two rotating surfaces of the cylinders 5 and 7. The FIGS. 6, 6A and 7 show a plan view and two cross sections taken through VIA—VIA and VII—VII respectively of the web N downstream of the pair of cylinders 5 and 7. FIGS. 6A and 7 clearly show the hole F and a strand of partially detached material indicated by A lying in the direction of advance of the material.

The strand A connected to each hole of the web N acts as a kind of nonreturn valve allowing the liquid to flow easily from the upper surface to the under surface of the web (with respect to the orientation shown in FIGS. 6 and 7), while it obstructs backflow in the opposite direction. When the web is used to form for example the outermost layer of a sanitary towel, as illustrated diagrammatically in FIG. 8, it is so placed that the strands are turned towards the interior of the towel, that is towards the body of absorbent material MA. In this way the liquid to be absorbed can easily flow from the outside to the inside of the towel whereas backflow in the opposite direction is practically prevented by the presence of the strands A.

The use of a plastic film for the web N offers the major advantage that the base material is practically impervious in areas without holes. As compared with a web formed by a membrane of carded fibers and/or any textile membranes, this reduces the risk of backflow of the liquid from the inside of the absorbent to the outside through the unbroken area of material N, that is the area without holes.

The use of a plastic film has the further advantage of eliminating the carding machine and/or other textile apparatuses from the production line on which the membrane is manufactured.

The method described can also be applied to composite webs, as mentioned earlier.

In certain particular applications, as for example in the manufacture of nappies for babies, it is expedient to have an outer layer that is permeable in a central area only, that is only where the urine is to flow. In the surrounding areas, however, it is expedient to prevent the passage of liquid in order to isolate the interior of the nappy from the exterior, thus avoiding any contact with the absorbed liquid. To this end, in an improved embodiment of the invention, the cylinder 7 may have areas—especially of complete or partial annular form—that are studded and annular areas that are smooth. In this case the web N that emerges from the pair of cylinders has perforated areas and nonperforated areas as illustrated diagrammatically in FIG. 9. In this figure N indicates a piece of web, that has perforated areas A1 and unbroken areas A2. In making the nappy, the web N is cut and wrapped around the body of internal absorbent material in such a way that a perforated strip or area A1 lies approximately along the center line of that surface of the happy which is intended to be placed against the user.

Figure 10:
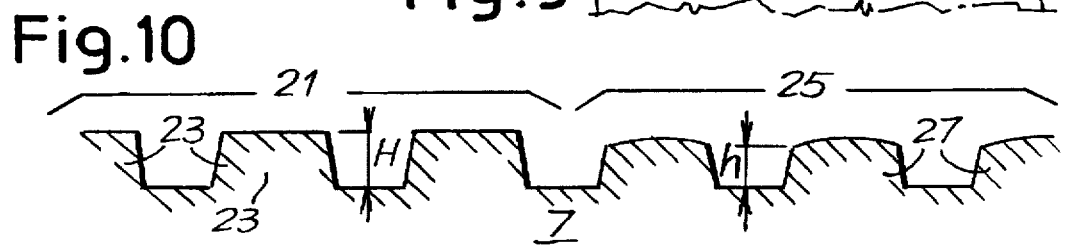
FIG. 10 shows a diagrammatic cross section of a portion of a cylinder provided with projections and suitable for producing a membrane or film with perforated areas bounded by non-perforated areas.

Instead of a cylinder having smooth areas and areas with projections, it is also possible to employ a cylinder having projections of differing heights, as diagrammatically indicated in FIG. 10, which shows a portion of the surface of the cylinder in a section taken through a plane passing through the axis. FIG. 10 shows an area 21 with protuberances 23 of height H, and an area 25, with protuberances 27 of height h, lower than H. The heights H and h are so determined that when the web N is rolled between the smooth cylinder 5 and the cylinder 7, perforations of the web are created in positions corresponding to the projections 23, while it is merely rolled in the area 25, with a resulting mutual sandwiching of the membranes of which it is composed, but is not perforated. The rolling between the surface of the cylinder 5 and the projections 27 does not over stiffen the material. The form shown in FIG. 10 can be made by, for example, uniform working of the surface of the cylinder 7 and then sandblasting those areas, such as 23, where the height of the projections 27 is to be reduced. Sandblasting results in projections 27 with a slightly rounded front surface, which gives an excellent action in use.

In a currently preferred embodiment, a polypropylene film has been used as the web. The linear pressure between the cylinders 5 and 7 has been set at 140 kg/cm and the percentage of slip at 18%. In other words, with a speed of advance of 40 m/min, the lower cylinder 5 turns at a peripheral speed equal to the speed of advance of the web N and the upper cylinder at a speed equal to 48 m/min. In this way excellent results have been obtained with the surface temperature of the cylinder 7 being maintained at approximately 120° C. and the temperature of the cylinder 5 at approximately 110° C.

I claim:

1. A method for forming a web that is permeable to liquids and designed to separate two environments and to allow liquid to flow in one direction from one of said environments to the other, said method including:

providing a web of material, providing two contra-rotating rollers, providing on one roller projections with outer surfaces, providing a smooth surface on the other roller, pressing said rollers together, rotating said rollers at different speeds whereby to provide a slipping action between the smooth surface of the one said other roller and the outer surfaces of the said projections on the said one roller, adjusting peripheral speed of the outer surface of the projections of the one roller to be greater than peripheral surface of the smooth surface of the other roller, feeding said web between said rollers at a speed slower than the peripheral speed of the outer surfaces of said projections, wherein the projections penetrate the web material and create holes in the material and also create a thickening of the web material by pushing web material from said holes and piling the web material up at a side of the holes while said web is in contact with said smooth roller.

2. The method of claim 1 wherein said web material is piled up ahead of the projections as the projections are moving across the smooth surface of the other roller.

3. The method of any one of claims 1 or 2 wherein the web material is a plastic film.

4. The method of any one of claims 1 or 2 wherein the web has a thickness and the pile of material at the sides of the holes has a height and the said height is at least 10 times the thickness of the web.

* * * * *